(12) United States Patent
Donovan

(10) Patent No.: US 8,012,730 B1
(45) Date of Patent: Sep. 6, 2011

(54) **SPECIFIC LYSIS OF *STAPHYLOCOCCAL* PATHOGENS BY BACTERIOPHAGE PHI11 ENDOLYSIN**

(75) Inventor: David M. Donovan, Baltimore, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 546 days.

(21) Appl. No.: 11/511,848

(22) Filed: Aug. 29, 2006

(51) Int. Cl.
*C12N 9/14* (2006.01)
*C07H 21/04* (2006.01)

(52) U.S. Cl. ..... 435/195; 435/183; 435/325; 435/252.3; 536/23.1; 536/23.2

(58) Field of Classification Search .................. None
See application file for complete search history.

(56) References Cited

U.S. PATENT DOCUMENTS 6,593,114 B1 * 7/2003 Kunsch et al. ............. 435/91.41

OTHER PUBLICATIONS

Ngo et al. in The Protein Folding Problem and Tertiary Structure Prediction, 1994, Merz et al. (ed.), Birkhauser, Boston, MA, pp. 433 and 492-495.*

Weerakoon et al. BPHHOLIN accession No. AAA99520.1 GI:511839, May 1996.*

Fischetti, Vincent A., "Bacteriophage lytic enzymes: novel anti-infectives," *Trends in Microbiology*, Oct. 2005, vol. 13, No. 10, pp. 491-496.

Loeffler, Jutta M. et al., "Rapid Killing of *Streptococcus pneumoniae* with a Bacteriophage Cell Wall Hydrolase," *Science*/www.sciencemag.org, Dec. 7, 2001, vol. 294, pp. 2170-2172.

Navarre, William Wiley et al., "Multiple Enzymatic Activities of the Murein Hydrolase From Staphylococcal Phage o11," *The Journal of Biological Chemistry*, May 28, 1999, vol. 274, No. 22, pp. 15847-15856.

Nelson, Daniel et al., "Prevention and elimination of upper respiratory colonization of mice by group A streptococci by using a bacteriophage lytic enzyme," *PNAS*, Mar. 27, 2001, vol. 98, No. 7, pp. 4107-4112.

Schuch, Raymond et al.,"A bacteriolytic agent that detects and kills *Bacillus anthracis*," *Nature*, Aug. 22, 2002, vol. 418, pp. 884-889.

Wang, Xin et al., "Analysis of a Peptidoglycan Hydrolase Gene from *Staphylococcus aureus* NCTC 8325," *Journal of Bacteriology*, Oct. 1992, vol. 174, No. 19, pp. 6303-6306.

* cited by examiner

*Primary Examiner* — Richard Hutson
(74) *Attorney, Agent, or Firm* — John D. Fado; Evelyn M. Rabin

(57) ABSTRACT

The *Staphylococcus aureus* bacteriophage phi11 endolysin has two peptidoglycan hydrolase domains (endopeptidase and amidase) and a SH3b cell wall-binding domain. In turbidity reduction assays, the purified protein can lyse untreated staphylococcal mastitis-causing pathogens, *S. aureus* and coagulase negative staphylococci (*S. chronogenes, S. epidermis, S. hyicus, S. simulans, S. warneri*, and *S. xylocus*), making it a strong antimicrobial protein and an effective candidate for treating multidrug-resistant staphylococci. Lytic activity is maintained at the pH (6.7) and the 'free' calcium concentration (3 mM) of milk. Truncated endolysin-derived proteins, containing just the endopeptidase domain, also lyse staphylococci, in the absence of the SH3b-binding domain.

9 Claims, 5 Drawing Sheets

SEQUENCE LISTING

<160> NUMBER OF SEQ ID NOS: 10

<210> SEQ ID NO 1
<211> LENGTH: 1367
<212> TYPE: DNA
<213> ORGANISM: Bacteriophage phi11

<400> SEQUENCE: 1

```
atgccaatgc tggttggaaa gttttgtttg gattacttct aaaaggttta ggtgcaaaag      60
atattccgtt cgctaacaac ttcgacggat tagctactgt ataccaaaat acaccggact     120
tcttagcaca acctggcgac atggtggtat tcggtagcaa ctacggtgct ggatatggtc     180
acgttgcatg ggtaattgaa gcaactttag attacatcat tgtatatgag cagaattggc     240
taggcggtgg ctggactgac ggaatcgaac aaccggctgg ggttgggaaa aagttacaag     300
acgacaacat gcttatgatt tccctatgtg gtttatccgt ccgaatttta aaagtgagac     360
agcgccacga tcagttcaat ctcctacaca agcaccctaa aaaagaaaca gctaagccac     420
aacctaaagc agtagaactt aaaatcatca agatgtggt taaaggttat gacctaccta     480
agcgtggtag taaccctaaa ggtatagtta tacacaacga cgcagggagc aaagggggcga     540 ctgctgaagc atatcgtaac ggattagtaa atgcacctt atcaagatta gaagcgggca     600
ttgcgcatag ttacgtatca ggcaacacag tttggcaagc cttagatgaa tcacaagtag     660
gttggcatac cgctaatcaa ataggtaata aatattatta cggtattgaa gtatgtcaat     720
caatgggcgc agataacgcg acattcttaa aaaatgaaca ggcaactttc caagaatgcg     780
ctagattgtt gaaaaaatgg ggattaccag caaacagaaa tacaatcaga ttgcacaatg     840
aatttacttc aacatcatgc cctcatagaa gttcggtttt acacactggt tttgacccag     900
taactcgcgg tctattgcca gaagacaagc ggttgcaact taaagactac tttatcaagc     960
agattagggc gtacatggat ggtaaaatac cggttgccac tgtctctaat gagtcaagcg    1020
cttcaagtaa tacagttaaa ccagttgcaa gtgcatggaa acgtaataaa tatggtactt    1080
actacatgga agaaagtgct agattcacaa acggcaatca accaatcaca gtaagaaaag    1140
tggggccatt cttatcttgt ccagtgggtt atcagttcca acctggtggg tattgtgatt    1200
atacagaagt gatgttacaa gatggtcatg tttgggtagg atatacatgg gaggggcaac    1260
gttattactt gcctattaga acatggaatg gttctgcccc acctaatcag atattaggtg    1320
acttatgggg agaaatcagt ctcgagcacc accaccacca ccactga                  1367
```

<210> SEQ ID NO 2
<211> LENGTH: 1088
<212> TYPE: DNA
<213> ORGANISM: Bacteriophage phi11

<400> SEQUENCE: 2

```
atgccaatgc tggttggaaa gttttgtttg gattacttct aaaaggttta ggtgcaaaag        60
atattccgtt cgctaacaac ttcgacggat tagctactgt ataccaaaat acaccggact       120
tcttagcaca acctggcgac atggtggtat tcggtagcaa ctacggtgct ggatatggtc       180
acgttgcatg ggtaattgaa gcaactttag attacatcat tgtatatgag cagaattggc       240
taggcggtgg ctggactgac ggaatcgaac aaccggctgg ggttgggaaa aagttacaag       300
acgacaacat gcttatgatt tccctatgtg gtttatccgt ccgaatttta aaagtgagac       360
agcgccacga tcagttcaat ctcctacaca agcaccctaa aaagaaaca gctaagccac        420 aacctaaagc agtagaactt aaaatcatca agatgtggt taaggttat gacctaccta        480 agcgtggtag taaccctaaa ggtatagtta tacacaacga cgcagggagc aaaggggcga       540
ctgctgaagc atatcgtaac ggattagtaa atgcaccttt atcaagatta gaagcgggca       600
ttgcgcatag ttacgtatca ggcaacacag tttggcaagc cttagatgaa tcacaagtag       660
gttggcatac cgctaatcaa ataggtaata atatattatta cggtattgaa gtatgtcaat       720
caatgggcgc agataacgcg acattcttaa aaaatgaaca ggcaactttc caagaatgcg       780
ctagattgtt gaaaaaatgg ggattaccag caaacagaaa tacaatcaga ttgcacaatg       840
aatttacttc aacatcatgc cctcatagaa gttcggtttt acacactggt tttgacccag       900
taactcgcgg tctattgcca gaagacaagc ggttgcaact aaagactac tttatcaagc        960 agattagggc gtacatggat ggtaaaatac cggttgccac tgtctctaat gagtcaagcg      1020
cttcaagtaa tacagttaaa ccagttgcaa gtgcatggaa actcgagcac caccaccacc      1080
accactga                                                               1088

<210> SEQ ID NO 3
<211> LENGTH: 503
<212> TYPE: DNA
<213> ORGANISM: Bacteriophage phi11

<400> SEQUENCE: 3
atgccaatgc tggttggaaa gttttgtttg gattacttct aaaaggttta ggtgcaaaag        60
atattccgtt cgctaacaac ttcgacggat tagctactgt ataccaaaat acaccggact       120
tcttagcaca acctggcgac atggtggtat tcggtagcaa ctacggtgct ggatatggtc       180
acgttgcatg ggtaattgaa gcaactttag attacatcat tgtatatgag cagaattggc       240
taggcggtgg ctggactgac ggaatcgaac aaccggctgg ggttgggaaa aagttacaag       300
acgacaacat gcttatgatt tccctatgtg gtttatccgt ccgaatttta aaagtgagac       360
agcgccacga tcagttcaat ctcctacaca agcaccctaa aaagaaaca gctaagccac        420 aacctaaagc agtagaactt aaaatcatca agatgtggt taaggttat gacctactcg        480 agcaccacca ccaccaccac tga                                              503

<210> SEQ ID NO 4
<211> LENGTH: 489
<212> TYPE: PRT
<213> ORGANISM: Bacteriophage phi11

<400> SEQUENCE: 4

Met Gln Ala Lys Leu Thr Lys Asn Glu Phe Ile Glu Arg Leu Lys Thr
1               5                   10                  15

Ser Glu Gly Lys Gln Phe Asn Val Asp Leu Trp Tyr Gly Phe Gln Cys
            20                  25                  30

Phe Asp Tyr Ala Asn Ala Gly Trp Lys Val Leu Phe Gly Leu Leu Leu
```

-continued

```
            35                  40                  45
Lys Gly Leu Gly Ala Lys Asp Ile Pro Phe Ala Asn Asn Phe Asp Gly
 50                  55                  60

Leu Ala Thr Val Tyr Gln Asn Thr Pro Asp Phe Leu Ala Gln Pro Gly
 65                  70                  75                  80

Asp Met Val Val Phe Gly Ser Asn Tyr Gly Ala Gly Tyr Gly His Val
                     85                  90                  95

Ala Trp Val Ile Glu Ala Thr Leu Asp Tyr Ile Val Tyr Glu Gln
                100                 105                 110

Asn Trp Leu Gly Gly Gly Trp Thr Asp Gly Ile Glu Gln Pro Ala Gly
                115                 120                 125

Val Gly Lys Lys Leu Gln Asp Asp Asn Met Leu Met Ile Ser Leu Cys
130                 135                 140

Gly Leu Ser Val Arg Ile Leu Lys Val Arg Gln Arg His Asp Gln Phe
145                 150                 155                 160

Asn Leu Leu His Lys His Pro Lys Lys Glu Thr Ala Lys Pro Gln Pro
                165                 170                 175

Lys Ala Val Glu Leu Lys Ile Ile Lys Asp Val Val Lys Gly Tyr Asp
                180                 185                 190

Leu Pro Lys Arg Gly Ser Asn Pro Lys Gly Ile Val Ile His Asn Asp
                195                 200                 205

Ala Gly Ser Lys Gly Ala Thr Ala Glu Ala Tyr Arg Asn Gly Leu Val
210                 215                 220

Asn Ala Pro Leu Ser Arg Leu Glu Ala Gly Ile Ala His Ser Tyr Val
225                 230                 235                 240

Ser Gly Asn Thr Val Trp Gln Ala Leu Asp Glu Ser Gln Val Gly Trp
                245                 250                 255

His Thr Ala Asn Gln Ile Gly Asn Lys Tyr Tyr Gly Ile Glu Val
                260                 265                 270

Cys Gln Ser Met Gly Ala Asp Asn Ala Thr Phe Leu Lys Asn Glu Gln
                275                 280                 285

Ala Thr Phe Gln Glu Cys Ala Arg Leu Leu Lys Lys Trp Gly Leu Pro
290                 295                 300

Ala Asn Arg Asn Thr Ile Arg Leu His Asn Glu Phe Thr Ser Thr Ser
305                 310                 315                 320

Cys Pro His Arg Ser Ser Val Leu His Thr Gly Phe Asp Pro Val Thr
                325                 330                 335

Arg Gly Leu Leu Pro Glu Asp Lys Arg Leu Gln Leu Lys Asp Tyr Phe
                340                 345                 350

Ile Lys Gln Ile Arg Ala Tyr Met Asp Gly Lys Ile Pro Val Ala Thr
                355                 360                 365

Val Ser Asn Glu Ser Ser Ala Ser Ser Asn Thr Val Lys Pro Val Ala
370                 375                 380

Ser Ala Trp Lys Arg Asn Lys Tyr Gly Thr Tyr Tyr Met Glu Glu Ser
385                 390                 395                 400

Ala Arg Phe Thr Asn Gly Asn Gln Pro Ile Thr Val Arg Lys Val Gly
                405                 410                 415

Pro Phe Leu Ser Cys Pro Val Gly Tyr Gln Phe Gln Pro Gly Gly Tyr
                420                 425                 430

Cys Asp Tyr Thr Glu Val Met Leu Gln Asp Gly His Val Trp Val Gly
                435                 440                 445

Tyr Thr Trp Glu Gly Gln Arg Tyr Tyr Leu Pro Ile Arg Thr Trp Asn
450                 455                 460
```

```
Gly Ser Ala Pro Pro Asn Gln Ile Leu Gly Asp Leu Trp Gly Glu Ile
465                 470                 475                 480

Ser Leu Glu His His His His His His
                485
```

<210> SEQ ID NO 5
<211> LENGTH: 396
<212> TYPE: PRT
<213> ORGANISM: Bacteriophage phi11

<400> SEQUENCE: 5

```
Met Gln Ala Lys Leu Thr Lys Asn Glu Phe Ile Glu Arg Leu Lys Thr
1               5                   10                  15

Ser Glu Gly Lys Gln Phe Asn Val Asp Leu Trp Tyr Gly Phe Gln Cys
                20                  25                  30

Phe Asp Tyr Ala Asn Ala Gly Trp Lys Val Leu Phe Gly Leu Leu Leu
            35                  40                  45

Lys Gly Leu Gly Ala Lys Asp Ile Pro Phe Ala Asn Asn Phe Asp Gly
50                  55                  60

Leu Ala Thr Val Tyr Gln Asn Thr Pro Asp Phe Leu Ala Gln Pro Gly
65                  70                  75                  80

Asp Met Val Val Phe Gly Ser Asn Tyr Gly Ala Gly Tyr Gly His Val
                85                  90                  95

Ala Trp Val Ile Glu Ala Thr Leu Asp Tyr Ile Val Tyr Glu Gln
            100                 105                 110

Asn Trp Leu Gly Gly Trp Thr Asp Gly Ile Glu Gln Pro Ala Gly
            115                 120                 125

Val Gly Lys Lys Leu Gln Asp Asp Asn Met Leu Met Ile Ser Leu Cys
130                 135                 140

Gly Leu Ser Val Arg Ile Leu Lys Val Arg Gln Arg His Asp Gln Phe
145                 150                 155                 160

Asn Leu Leu His Lys His Pro Lys Lys Glu Thr Ala Lys Pro Gln Pro
                165                 170                 175

Lys Ala Val Glu Leu Lys Ile Ile Lys Asp Val Val Lys Gly Tyr Asp
            180                 185                 190

Leu Pro Lys Arg Gly Ser Asn Pro Lys Gly Ile Val Ile His Asn Asp
            195                 200                 205

Ala Gly Ser Lys Gly Ala Thr Ala Glu Ala Tyr Arg Asn Gly Leu Val
210                 215                 220

Asn Ala Pro Leu Ser Arg Leu Glu Ala Gly Ile Ala His Ser Tyr Val
225                 230                 235                 240

Ser Gly Asn Thr Val Trp Gln Ala Leu Asp Glu Ser Gln Val Gly Trp
                245                 250                 255

His Thr Ala Asn Gln Ile Gly Asn Lys Tyr Tyr Gly Ile Glu Val
            260                 265                 270

Cys Gln Ser Met Gly Ala Asp Asn Ala Thr Phe Leu Lys Asn Glu Gln
            275                 280                 285

Ala Thr Phe Gln Glu Cys Ala Arg Leu Leu Lys Lys Trp Gly Leu Pro
290                 295                 300

Ala Asn Arg Asn Thr Ile Arg Leu His Asn Glu Phe Thr Ser Thr Ser
305                 310                 315                 320

Cys Pro His Arg Ser Ser Val Leu His Thr Gly Phe Asp Pro Val Thr
                325                 330                 335

Arg Gly Leu Leu Pro Glu Asp Lys Arg Leu Gln Leu Lys Asp Tyr Phe
            340                 345                 350
```

```
Ile Lys Gln Ile Arg Ala Tyr Met Asp Gly Lys Ile Pro Val Ala Thr
        355                 360                 365
Val Ser Asn Glu Ser Ser Ala Ser Ser Asn Thr Val Lys Pro Val Ala
    370                 375                 380
Ser Ala Trp Lys Leu Glu His His His His His His
385                 390                 395
```

<210> SEQ ID NO 6
<211> LENGTH: 201
<212> TYPE: PRT
<213> ORGANISM: Bacteriophage phi11

<400> SEQUENCE: 6

```
Met Gln Ala Lys Leu Thr Lys Asn Glu Phe Ile Glu Arg Leu Lys Thr
1               5                   10                  15
Ser Glu Gly Lys Gln Phe Asn Val Asp Leu Trp Tyr Gly Phe Gln Cys
                20                  25                  30
Phe Asp Tyr Ala Asn Ala Gly Trp Lys Val Leu Phe Gly Leu Leu Leu
            35                  40                  45
Lys Gly Leu Gly Ala Lys Asp Ile Pro Phe Ala Asn Asn Phe Asp Gly
    50                  55                  60
Leu Ala Thr Val Tyr Gln Asn Thr Pro Asp Phe Leu Ala Gln Pro Gly
65                  70                  75                  80
Asp Met Val Val Phe Gly Ser Asn Tyr Gly Ala Gly Tyr Gly His Val
                85                  90                  95
Ala Trp Val Ile Glu Ala Thr Leu Asp Tyr Ile Ile Val Tyr Glu Gln
            100                 105                 110
Asn Trp Leu Gly Gly Gly Trp Thr Asp Gly Ile Glu Gln Pro Ala Gly
        115                 120                 125
Val Gly Lys Lys Leu Gln Asp Asp Asn Met Leu Met Ile Ser Leu Cys
    130                 135                 140
Gly Leu Ser Val Arg Ile Leu Lys Val Arg Gln Arg His Asp Gln Phe
145                 150                 155                 160
Asn Leu Leu His Lys His Pro Lys Lys Glu Thr Ala Lys Pro Gln Pro
                165                 170                 175
Lys Ala Val Glu Leu Lys Ile Ile Lys Asp Val Val Lys Gly Tyr Asp
            180                 185                 190
Leu Leu Glu His His His His His His
        195                 200
```

<210> SEQ ID NO 7
<211> LENGTH: 26
<212> TYPE: DNA
<213> ORGANISM: Unknown
<220> FEATURE:
<223> OTHER INFORMATION: Chemically Synthesized

<400> SEQUENCE: 7
gtggcgcata tgcaagcaaa attaac                                          26

<210> SEQ ID NO 8
<211> LENGTH: 25
<212> TYPE: DNA
<213> ORGANISM: Unknown
<220> FEATURE:
<223> OTHER INFORMATION: Chemically Synthesized

<400> SEQUENCE: 8
tgactatgtc ctcgagactg atttc                                           25

```
<210> SEQ ID NO 9
<211> LENGTH: 21
<212> TYPE: DNA
<213> ORGANISM: Unknown
<220> FEATURE:
<223> OTHER INFORMATION: Chemically Synthesized

<400> SEQUENCE: 9
actaccacgc tcgagtaggt c                                              21

<210> SEQ ID NO 10
<211> LENGTH: 27
<212> TYPE: DNA
<213> ORGANISM: Unknown
<220> FEATURE:
<223> OTHER INFORMATION: Chemically Synthesized

<400> SEQUENCE: 10
agtaccatat ttctcgagtt tccatgc                                        27
```

SPECIFIC LYSIS OF *STAPHYLOCOCCAL* PATHOGENS BY BACTERIOPHAGE PHI11 ENDOLYSIN

BACKGROUND OF THE INVENTION

1. Field of the Invention

This invention relates to a nucleic acid encoding a functional module or domain of a particular peptidoglycan hydrolase, i.e., the phi11 endolysin, a protein which specifically attacks the peptidoglycan cell wall of untreated *S. aureus* and coagulase negative staphylococci (*S. chronogenes, S. epidermis, S. hyicus, S. simulans, S. warneri,* and *S. xylocus*). The phi11 endolysin is active over a broad range of physiological conditions including the pH and calcium concentration of bovine milk. The invention further relates to methods of treating diseases caused by the bacteria for which the phi11 endolysin is specific.

2. Description of the Relevant Art

Bovine mastitis, an infection of the mammary gland, exists on every dairy farm, often with one third of the animals affected. This world wide problem costs two billion dollars annually to the USA dairy industry (Sordillo et al. 2002. *J. Mammary Gland Biol. Neoplasia* 7(2): 135-146). Coagulase-negative staphylococci (CNS) and *Staphylococcus aureus* are major mastitis pathogens in the United States; they were determined to be responsible for 22% and 18%, respectively, of the mastitis cases in a study of New York and Pennsylvania dairy herds (Wilson et al. 1997. *J. Dairy Sci.* 80: 2592-2598). Antibiotics are the standard treatment for mastitis, but such treatment is often less than 50% effective, a situation which, at times, results in premature culling (Deluyker et al. 2005. *J. Dairy Sci.* 88: 604-614).

Antibiotic resistance in mastitis treatment is of concern because mastitis is the single most common reason for antimicrobial use in dairy herds (Erskine et al. 2002. *J. Dairy Sci.* 85 (5): 1111-1118). In a broad study of nine European countries, the USA, and Zimbabwe, 57% of 811 *S. aureus* isolates from bovine mastitis showed resistance to penicillin (De Oliveira et al. 2001. *J. Dairy Sci.* 83(4): 855-862). Likewise, 44% of the mastitis strains identified in an Ohio study demonstrated resistance to at least one antibiotic (Rajala-Schultz et al. 2004. *Vet. Microbiol.* 102 (1-2): 33-42). The Food and Drug Administration (FDA), the United States Department of Agriculture (USDA) and the Center for Disease Control (CDC) promote the development of antimicrobials that reduce risk of resistance development (CDC Action Plan: http://www.cdc.gov/drugresistance/actionplan/html/product.htm). The use of pathogen-specific antimicrobials is expected to reduce the incidence of resistance development (Nathan, C. 2004. Nature 431: 899-902; Walsh, C. 2003. Nat. Rev. Microbiol. 1 (1): 65-70).

To reduce the use of broad range antibiotics and thus decrease the chance of antibiotic resistance development, our goal is to develop pathogen-specific agents that are effective for the treatment of mastitis and as well as for the treatment of clinical multidrug-resistant bacteria, in particular staphylococci, that have developed resistance to antimicrobial drugs. Methicillin/oxacillin-resistant *S. aureus* is an example of such multi-drug resistant staphylococci. Thus, the invention relates to the protein phi11 endolysin which is specific for and has exolytic activity (i.e., degrades the peptidoglycan of the bacterial cell when exposed externally resulting in lysis of the cell) toward untreated *S. aureus* and coagulase-negative staphylococci. Further, the invention relates to methods of treating diseases caused by the bacteria for which phi11 endolysin is specific. An additional goal is to express the gene encoding phi11 endolysin and truncated endolysin molecules in mammary glands of transgenic cattle (Donovan et al. 2005. *Transgenic Res.* 14 (5): 563-567; Wall et al. 2005. *Nat. Biotechnol.* 23: 445-451). Therefore, both approaches, a strategy of developing transgenic cattle comprising nucleic acid molecules encoding complete and truncated phi11 endolysin and a strategy focused on treatments with phi11 endolysin polypeptide compositions, are important tools for clinical success.

Bacteriophage endolysins specifically degrade the peptidoglycan (PG) of their host cell wall, thus lysing the bacteria, and allowing infective phage to escape. Each phage infects a single cell, replicates itself within the host cell, and then lyses the host cell releasing the progeny phage which then go on to repeat the cycle. Each phage genome codes for lytic proteins that degrade the bacterial cell wall peptidoglycan and allow the newly replicated phage to escape. Although peptidoglycan structure is similar between species, with the oligosaccharide backbone present in all, there is also a great deal of cell wall diversity between different bacterial species. Bacteriophage endolysins are of interest as antimicrobials against Gram-positive organisms (Loessner, M. J. 2005. *Curr. Opin. Microbiol.* 8 (4): 480-487) due to their high host-specificity and to reports that Gram-positive bacteria are highly unlikely to develop resistance to the peptidoglycan hydrolyzing action of their bacteriophage endolysins (Loeffler et al. 2001. *Science* 294: 2170-2172; Schuch et al. 2002. Nature 418: 884-889). Peptidoglycan hydrolases have been proposed for human antimicrobial applications (Schuch et al., supra; Fischetti, V. A. 2003. *Ann. N.Y. Acad. Sci.* 987: 207-214; Fischetti, V. A. 2005. *Trends Microbiol.* 13: 491-496), and have demonstrated efficacy in mouse models of human disease (Cheng et al. 2005. *Antimicrob. Agents Chemother.* 49: 111-117; Jado et al. 2003. *J. Antimicrob. Chemother.* 52 (6): 967-973; Nelson et al. 2001. *Proc. Natl. Acad. Sci. U.S.A.* 98 (7): 4107-4112), as well as in transgenic murine (Kerr et al. 2001. *Nat. Biotech.* 19: 66-70) and bovine (Wall et al., supra) mammary glands.

There are at least three peptidoglycan hydrolase activities which have been identified in endolysins: glycosidase, amidase and endopeptidase, (Lopez and Garcia. 2004. *FEMS Microbiol. Rev.* 28: 553-580). They are encoded by highly conserved domains; each cleaves a unique peptidoglycan bond (Loessner, supra). The conserved domains are ~200 amino acids in size (Huard et al. 2003. *Microbiology* 149 (Pt 3): 695-705; Rigden et al. 2003. *Trends Biochem. Sci.* 28: 230-234; Bateman and Rawlings. 2003. *Trends Biochem. Sci.* 28: 234-237), and are readily identified using common domain databases (Uniprot: http://www.pir.uniprot.org/index.shtml; Pfam: http://www.sange.ac.uk/cgi-bin/Pfam/getacc?PF04650; SMART: http://smart.embl-heidelberg.de/, or NCBI conserved domain data base). The domains are referred to as modules because they can often function independently of the remainder of the native endolysin (Navarre et al. 1999. *J. Biol. Chem.* 274 (22): 15847-15856; Yokoi et al. 2005. *Gene* 351: 97-108; Morita et al. 2001. *FEBS Lett.* 500: 56-59; Donovan et al. 2006b. *Appl. Environ. Microbiol.* 72: 5108-5112), and maintain activity when fused to create novel, recombinant, fusion hydrolases (Diaz et al. 1990. *Proc. Natl. Acad. Sci. USA* 87:8125-8129; Garcia et al. 1990. *Gene* 86: 81-88; Donovan et al. 2006 a. *Appl. Environ. Microbiol.* 72: 2988-2996).

In the quest for antimicrobials against multidrug-resistant staphylococci including, for example, mastitis-causing bacteria and methicillin/oxacillin-resistant *S. aureus*, agents must be found that can target our pest organisms very specifically. This is not just to reduce the potential for resistance development, but also to prevent damage to commercially important organisms that are necessary for the downstream processing of milk into yogurt and cheese. The prevention of infection and disease caused by multidrug-resistant organisms, including mastitis, would not just benefit animal health, and food quality, but also human health. Any antimicrobial that is specific for a given pathogen will potentially reduce the use of broad range antibiotics and thus also help prevent the onslaught of multi drug resistant varieties.

Thus, to counter the rise of drug resistant pathogenic bacteria, there is a need for new specific antimicrobial treatments. Reagents shown to be very specific for the genera, species or substrains of concern would give better effective control of economically important diseases and therefore are ideal candidates for therapeutic treatments.

SUMMARY OF THE INVENTION

We have discovered that the nucleic acid encoding phi11 endolysin, a protein which specifically attacks the peptidoglycan cell wall of untreated *S. aureus* and coagulase negative staphylococci can be truncated and that phi11 endolysin, and also truncations of phi11 endolysin, can be used as an antimicrobial treatment for mastitis as well as for infection and for other human diseases, such as infection and disease caused by multidrug-resistant staphylococci.

In accordance with this discovery, it is an object of the invention to provide nucleic acid molecules encoding phi11 endolysin or truncated phi11 endolysin polypeptides.

It is also an object of the invention to provide an antimicrobial phi11 endolysin or a truncated phi11 endolysin, which is functional, i.e., retains its properties for degrading the peptidoglycan cell wall of the Gram-positive bacteria.

An added object of the invention is to provide a nucleic acid sequence encoding phi11 endolysin or truncated phi11 endolysin polypeptides according to the invention as an encoding sequence which allows disease resistance to be imparted to the organism. It is well understood that this sequence can also be used in combination with another sequence, or sequences, encoding one or more disease resistant properties.

It is an object of the invention to provide a nucleic acid sequence encoding phi11 endolysin or truncated phi11 endolysin polypeptides according to the invention as an encoding sequence which can be expressed in the mammary glands of transgenic cattle.

It is a further object of the invention to provide a nucleic acid encoding an antimicrobial fusion protein formed from a nucleic acid encoding a functional module or domain of the phi11 endolysin, a protein which specifically attacks the peptidoglycan cell wall of untreated *S. aureus* and coagulase negative staphylococci in combination with nucleic acid encoding a functional module(s) or domain(s) of another endolysin(s) having a different hydrolase activity, e.g., glycosidase, amidase and endopeptidase activity.

A still further object of the invention also relates to a chimeric gene (or expression cassette) comprising an encoding sequence as well as heterologous regulatory elements in positions 5' and 3' which can function in a host organism, the encoding sequence comprising at least one nucleic acid sequence encoding an antimicrobial phi11 endolysin or a truncated phi11endolysin.

An additional object of the invention is to provide a host organism into which the phi11 gene, or truncated gene, according to the invention can be introduced so as to produce an endolysin or truncated endolysin.

An added object of the invention is to provide compositions useful for the treatment of disease caused by the bacteria for which the phi11 endolysin and truncated phi11 endolysin are specific.

Also part of this invention is a kit, comprising a composition for treatment of disease caused by the bacteria for which the phi11 endolysin and truncated phi11 endolysin are specific.

Other objects and advantages of this invention will become readily apparent from the ensuing description.

BRIEF DESCRIPTION OF THE DRAWINGS

FIG. 2A depicts the analysis of nickel column-purified phi11 endolysin-derived proteins. Lanes: M, Markers; 1, phi11-481; 2, phi11-389; 3, phi11-194. Carets indicate phi11-derived proteins. FIG. 2B depicts results of the turbidity assay and shows that 25 µg of partially purified endolysin-derived proteins are active against *S. aureus* (black bars). There is no activity against *Streptococcus agalactiae* (open bars). Specific Activity ($OD_{600nm}$/mg/min). Extracts from *E. coli* harboring just pET21a vector do not have lytic activity in the turbidity assays against *S. agalactiae* or *S. aureus* (data not shown).

DETAILED DESCRIPTION OF THE INVENTION

Figure 1:
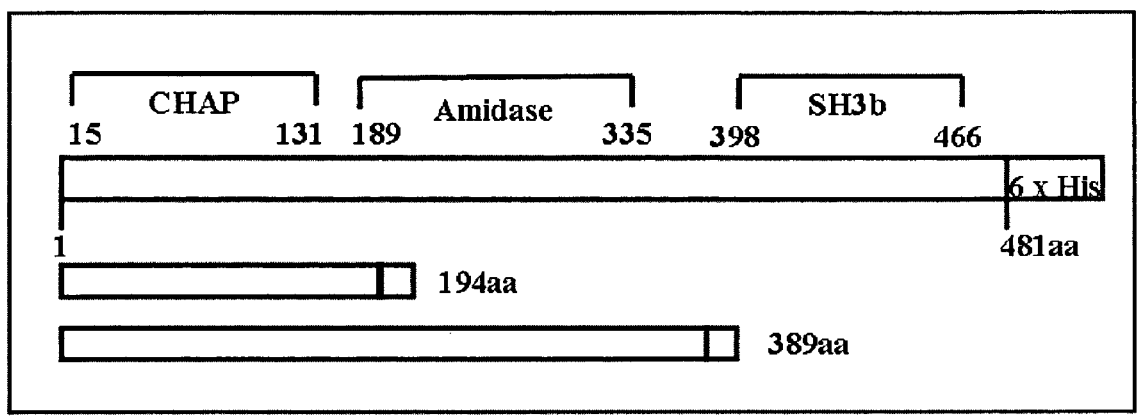
FIG. 1 depicts a schematic of phi11 endolysin protein structure and deletion constructs. Phi11 194 and phi11 389 deletion constructs are illustrated, along with the approximate location of the CHAP, amidase and SH3b cell wall-binding domains. All constructs also contain a 6× Histidine residue ("His tag") encoded for at the C-terminus of the resultant proteins for use in purification via nickel column chromatography.

The increased incidence of bacterial antibiotic resistance has led to a renewed search for novel antimicrobials. This invention relates to the *S. aureus* (NCTC 8325) phi11 prophage endolysin gene which was first isolated from the *S. aureus* genome as the LytA amidase (Wang et al. 1991. *Gene* 102: 105-109) and later shown to be a phage lytic enzyme. It contains two peptidoglycan hydrolase activities, a cysteine, histidine-dependent amidohydrolases/peptidase (CHAP) endopeptidase (Bateman and Rawlings, supra; Rigden et al., supra) that cleaves at D-alanyl-glycyl moieties and an N-acetylmuramyl-L-alanyl-glycyl amidase module (Navarre et al., supra) as well as a SH3b cell wall-binding domain (Baba and Schneewind. 1998. *EMBO J.* 17: 4639-4646).

Bacteriophage endolysins, as described above, are bacteriophage-encoded enzymes which degrade the peptidoglycan component of the bacterial cell wall to allow the bacteriophage to escape. Endolysins usually attack the peptidoglycan from inside the cell wall, where they are released during cell lysis by the bacteriophage. However, it was shown that exposure of susceptible bacteria to preparations of the endolysin are often sufficient to lyse Gram-positive bacteria from the outside in both in vitro and in vivo settings (Nelson et al. 2001. *Proc. Natl. Acad. Sci. U.S.A.* 98 (7): 4107-4112; Schuch et al. 2002. *Nature* 418(6900): 884-889; Loeffler et al. 2001. *Science* 294(5549): 21270-21272). The peptidoglycan lytic activities of peptidoglycan hydrolases (endolysins) (N-acetylmuramidases, N-acetylglucosaminidases, N-acetylmuramyl-L-alanine amidases, and endopeptidases) have been localized to short modular domains (~100-200 amino acids), any one of which is sufficient to lyse the host cell. Endolysin substrate binding domains have been characterized via fusions of endolysin modules (Lopez et al., supra).

The *S. aureus* phi11 endolysin has both an amidase and an endopeptidase domain that are specific for and have been shown to be enzymatically active on cell wall preparations of *S. aureus* (Navarre et al., supra). Previous work of Navarre et al. created a deletion construct which removed the amidase mid-region of the protein and fused the N-terminal CHAP endopeptidase to the C-terminal SH3b binding domain. This work demonstrated that the CHAP domain did not require the amidase domain for enzymatic activity. However, the study did not determine whether the SH3b domain was required for activity and specificity of the CHAP domain, nor did it demonstrate exolytic activity on living cells. The bacterial cell wall preparations of Navarre, as well as those of other studies, had been autoclaved or treated with SDS prior to their exposure to endolysin treatment.

We have demonstrated that the phi11 endolysin-derived protein and truncated versions of the endolysin have exolytic activity toward untreated *S. aureus* and mastitis-causing coagulase-negative staphylococci, and that the endolysin is active at the physiological pH and calcium concentrations found in milk. Characterization of a truncated phi11 endolysin, i.e., phi11-194, demonstrated that the CHAP domain is sufficient to lyse untreated *S. aureus* cells without a need for either the amidase domain or the SH3b domain.

The *S. warnei* M phage phi WMY endolysin (lysWMY) is weakly homologous to phi11 endolysin (only 43% identical to the phi11 endolysin) has a similar domain organization [N-terminal CHAP endopeptidase—amidase—C-terminal SH3b]. Site-directed and deletion mutagenesis analysis demonstrated that both the CHAP endopeptidase domain and the amidase domain of the phi WMY endolysin contribute to degradation of autoclaved staphylococci as evidenced by SDS-PAGE zymogram results. The lysWMY CHAP domain has lytic activity towards several SDS-treated staphylococci in zymograms, including many CNS and *S. aureus* (Yokoi et al., supra). Despite knowledge of the peptidoglycan hydrolase enzymatic activities of this and other *S. aureus* bacteriophage endolysins from studies demonstrating lysis of autoclaved and SDS-treated staphylococcal cell walls, only one published phage endolysin, LysK, has been shown to lyse untreated staphylococci, including many coagulase negative staphylococci (CNS) and clinically relevant, multi-drug resistant strains of *S. aureus*, in a plate lysis assay (O'flaherty et al. 2005. *J. Bacteriol.* 187: 7161-7164). LysK shares a similar modular organization; however, LysK is distinct from phi11 and shares only 37% identity with phi 11.

For use as an anti-mastitis agent and for use more generally to combat disease caused by drug-resistant staphylococci, it is essential that the endolysin have exolytic activity. It is also important to our project that the antimicrobial be specific to its pathogen group. The broad range antibiotics pirlimyacin and penicillin are widely used in the treatment of mastitis (Cattell et al. 2001. *J. Daily Sci.* 84: 2036-2043); however, they are often less than 50% successful (Deluyker et al., supra). Further, use of such broad range antimicrobials is discouraged due to concerns that antibiotic resistance among mastitis pathogens is on the rise (Werkenthin et al. 2001. *Vet. Res.* 32:341-362; Rajala-Schultz et al., supra) and to fear that such strains might find their way from the farm to the clinic (Ferber, D. 2002. Science 295: 27-28; Ferber, D. 2003. Science 301: 1027). To reduce concerns about antimicrobial resistance among mastitis pathogens, it is our goal to identify protein antimicrobials that do not have activity against a broad range of pathogens but rather are pathogen-specific (or lyse only closely related species). We have shown that neither the full length nor truncated phi11 endolysin constructs will lyse *Streptococcus agalactiae*; see Example 4 for turbidity reduction assay results.

Similarly, it is important that an antimicrobial effective for treating mastitis-causing bacteria also be effective in a milk environment. We have characterized the full length phi11-481 endolysin and demonstrate antimicrobial activity at both the pH (6.7) and free-calcium concentration (3 mM) consistent with milk (Neville et al. 1994. *J. Dairy Sci.* 77: 1964-1975). Such activity is comparable to that of lysostaphin (data not shown) and is encouraging because lysostaphin has a proven record of preventing *S. aureus* mammary infections in transgenic mammary glands in mice (Kerr et al., supra) and cattle (Wall et al., supra).

Although the results of lysostaphin expression in transgenic cattle and mice are encouraging, we believe that the phi11 endolysin is a potentially better candidate for treating mastitis and infection and disease caused by multidrug-resistant staphylococci for several reasons. First, it is known that lysostaphin has a single endopeptidase function, that of cleaving glycyl-glycyl bonds of the peptidoglycan peptide cross bridge (Browder et al. 1965. *Biochem. BioPhys. Res. Comm.* 19: 383-389) and that strains have developed resistance to this activity by inserting serines into the cross bridge (Thumm et al. 1997. *Mol. Microbiol.* 23: 1251-1265). Second, the phi11 endolysin potentially has two putative antimicrobial activities: an endopeptidase and an amidase. For a pathogen to develop resistance to two enzymatic activities, it is known that two simultaneous compensatory mutations in the same cell would be required, and it is believed that such an event would be rare. Third, it is reported that, through the coevolution of bacteriophage and their hosts, the bacteriophage endolysins target essential bonds in the peptidoglycan, such that despite significant effort to find them, no resistant strains have been identified to those phage endolysins which have been screened (Loeffler et al., supra).

The sequences encoding the phi11 prophage endolysin are of bacteriophage origin. The nucleic acid sequences encoding the phi11 endolysin-derived proteins phi11-481, phi11-389, and phi11-194 are identified by SEQ ID NO:1, SEQ ID NO:2, and SEQ ID NO:3, respectively. These sequences include the nucleotides encoding the six histidine tag required for purification. The amino acid sequence of the phi11 endolysin-derived protein phi11-481 is identified by SEQ ID NO:4. The truncated endolysin proteins, phi11-389 and phi11-194 are identified by SEQ ID NO:5 and SEQ ID NO:6, respectively. The encoding sequences of the individual modules of the phi11 prophage endolysin according to the invention can be assembled by any usual method for constructing and assembling nucleic acid fragments which are well known to those skilled in the art and widely described in the literature and illustrated especially by the use examples of the invention.

Another subject of the invention is the use of a nucleic acid sequence encoding a phi11 prophage endolysin according to the invention as an encoding sequence which allows disease resistance to be imparted to the organism. It is well understood that this sequence can also be used in combination with another sequence, or sequences, encoding one or more disease resistant properties. The present invention therefore also relates to a strategy of generating a nucleic acid sequence encoding a chimeric endolysin according to the invention, this process being defined herein.

The present invention also relates to a chimeric gene (or expression cassette) comprising an encoding sequence as well as heterologous regulatory elements in positions 5' and 3' which can function in a host organism, the encoding sequence comprising at least one nucleic acid sequence encoding a phi11 prophage endolysin related protein (truncation or fusion) as defined above. By host organism there is to be understood any single-celled or lower or higher non-human multi-celled organism into which phi11 prophage endolysin gene according to the invention can be introduced. The regulatory elements required for expressing the nucleic acid sequence encoding a phi11 prophage endolysin are well known to those skilled in the art and depend on the host organism. The means and methods for identifying and choosing the regulatory elements are well known to those skilled in the art and widely described in the literature.

The present invention also relates to a cloning and/or expression vector for transforming a host organism containing at least the phi11 prophage endolysin gene as defined hereinabove. This vector comprises, in addition, to the above phi11 prophage endolysin gene, at least one replication origin. This vector can be constituted by a plasmid, a cosmid, a bacteriophage or a virus which is transformed by introducing the chimeric gene according to the invention. Such transformation vectors according to the host organism to be transformed are well known to those skilled in the art and widely described in the literature.

A further subject of the invention is a process for the transformation of host organisms, by integrating a least one nucleic acid sequence or chimeric gene as defined hereinabove, which transformation may be carried out by any suitable known means which have been widely described in the specialist literature and in particular in the references cited in the present application, more particularly by the vector according to the invention.

According to the present invention, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof. This will also include a DNA sequence for which the codons encoding the phi11 prophage endolysin according to the invention will have been optimized according to the host organism in which it will be expressed, these optimization methods being well known to those skilled in the art.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "transgene" is understood to describe genetic material which has been or is about to be artificially inserted into the genome of a non-human animal, and particularly into a cell of a living non-human mammal. It is to be understood that as used herein the term "transgenic" includes any cell, cell line, or tissue, the genotype of which has been altered by the presence of a heterologous nucleic acid including those transgenics initially so altered as well as those created by sexual crosses or asexual propagation from the initial transgenic.

The term "transformation" refers to a permanent or transient genetic change induced in a cell following the incorporation of new DNA (i.e. DNA exogenous to the cell). Where the cell is a mammalian cell, a permanent genetic change is generally achieved by introduction of the DNA into the genome of the cell. When the cell is a bacterial cell, the term usually refers to an extrachromosomal, self-replicating vector which harbors a selectable antibiotic resistance. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell.

The term "construct" refers to a recombinant nucleic acid, generally recombinant DNA, that has been generated for the purpose of the expression of a specific nucleotide sequence(s), or is to be used in the construction of other recombinant nucleotide sequences. A "construct" or "chimeric gene construct" refers to a nucleic acid sequence encoding a protein, operably linked to a promoter and/or other regulatory sequences.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter) or a DNA sequence and a regulatory sequence(s) are connected in such a way as to permit gene expression when the appropriate molecules (e.g., transcriptional activator proteins) are bound to the regulatory sequence(s).

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter.

The term "cDNA" refers to all nucleic acids that share the arrangement of sequence elements found in native mature mRNA species, where sequence elements are exons and 3' and 5' non-coding regions. Normally mRNA species have contiguous exons, with the intervening introns removed by nuclear RNA splicing, to create a continuous open reading frame encoding the protein. "cDNA" refers to a DNA that is complementary to and derived from an mRNA template.

The term "genomic sequence" refers to a sequence having non-contiguous open reading frames, where introns interrupt the protein coding regions. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I. and II (Ed. D. N. Glover), IRL Press, Oxford, 1985. "Recombinant," as used herein, does not refer to naturally occurring genetic recombinations.

As used herein, the term "chimeric" refers to two or more DNA molecules which are derived from different sources, strains, or species, which do not recombine under natural conditions, or to two or more DNA molecules from the same species, which are linked in a manner that does not occur in the native genome.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

A "protein" or "polypeptide" is a chain of amino acids arranged in a specific order determined by the coding sequence in a polynucleotide encoding the polypeptide. Each protein or polypeptide has a unique function.

The invention includes functional phi11 prophage endolysin polypeptide and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of phi11 prophage endolysin" refers to all fragments of phi11 prophage endolysin that retain phi11 prophage endolysin activity and function to lyse staphylococcal bacteria.

Modifications of the phi11 prophage endolysin primary amino acid sequence may result in further mutant or variant proteins having substantially equivalent activity to the phi11 prophage endolysin polypeptides described herein. Such modifications may be deliberate, as by site-directed mutagenesis, or may occur by spontaneous changes in amino acid sequences where these changes produce modified polypeptides having substantially equivalent activity to the phi11 prophage endolysin polypeptide. Any polypeptides produced by minor modifications of the phi11 prophage endolysin primary amino acid sequence are included herein as long as the biological activity of phi11 prophage endolysin is present; e.g., having a role in pathways leading to lysis of staphylococcal bacteria.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a host cell may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. Nucleic Acid Hybridization, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. An indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein. Thus, isolated sequences that encode a phi11 prophage endolysin polypeptide and which hybridize under stringent conditions to the phi11 prophage endolysin sequences disclosed herein, or to fragments thereof, are encompassed by the present invention.

Substantially similar nucleic acid fragments of the instant invention may also be characterized by the percent identity of the amino acid sequences that they encode to the amino acid sequences disclosed herein, as determined by algorithms commonly employed by those skilled in this art. Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

A "substantial portion" of an amino acid or nucleotide sequence comprises an amino acid or a nucleotide sequence that is sufficient to afford putative identification of, the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular plant protein. The skilled artisan, having the benefit of the sequences as reported herein, may now use all or a substantial portion of the disclosed sequences for purposes known to those skilled in this art. Thus, such a portion represents a "substantial portion" and can be used to establish "substantial identity", i.e., sequence identity of at least 80%, compared to the reference sequence. Accordingly, the instant invention comprises the complete sequences as reported in the accompanying Sequence Listing, as well as substantial portions at those sequences as defined above.

Fragments and variants of the disclosed nucleotide sequences and proteins encoded thereby are also encompassed by the present invention. By "fragment" a portion of the nucleotide sequence or a portion of the amino acid sequence and hence protein encoded thereby is intended. Fragments of a nucleotide sequence may encode protein fragments that retain the biological activity of the native protein and hence have phi11 prophage endolysin-like activity. Alternatively, fragments of a nucleotide sequence that are useful as hybridization probes may not encode fragment proteins retaining biological activity.

By "variants" substantially similar sequences are intended. For nucleotide sequences, conservative variants include those sequences that, because of the degeneracy of the genetic code, encode the amino acid sequence of one of the phi11 prophage endolysin polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, phi11 prophage endolysin activity as described herein. Such variants may result from, for example, genetic polymorphism or from human manipulation. Biologically active variants of a native phi11 prophage endolysin protein of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired phi11 prophage endolysin activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of phi11 prophage endolysin protein can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

The staphylococcal control compositions of the invention comprise the antimicrobial composition of the invention dissolved or suspended in an aqueous carrier or medium. The composition may further generally comprise an acidulant or admixture, a rheology modifier or admixture, a film-forming agent or admixture, a buffer system, a hydrotrope or admixture, an emollient or admixture, a surfactant or surfactant admixture, a chromophore or colorant, and optional adjuvants. The preferred compositions of this invention comprise ingredients which are generally regarded as safe, and are not of themselves or in admixture incompatible with milk or milk by-products or human and veterinary applications. Likewise, ingredients may be selected for any given composition which are cooperative in their combined effects whether incorporated for antimicrobial efficacy, physical integrity of the formulation or to facilitate healing and health in medical and veterinary applications, including for example in the case of mastitis, healing and health of the teat. or other human or animal body part. Generally, the composition comprises a carrier which functions to dilute the active ingredients and facilitates stability and application to the intended surface. The carrier is generally an aqueous medium such as water, or an organic liquid such as an oil, a surfactant, an alcohol, an ester, an ether, or an organic or aqueous mixture of any of these. Water is preferred as a carrier or diluent in compositions of this invention because of its universal availability and unquestionable economic advantages over other liquid diluents.

Avoiding the generalized use of broad range antimicrobials and using highly specific antimicrobials for just the target organisms involved, should help reduce the ever-increasing incidence of antibiotic resistance.

EXAMPLES

Having now generally described this invention, the same will be better understood by reference to certain specific examples, which are included herein only to further illustrate the invention and are not intended to limit the scope of the invention as defined by the claims.

Example 1

Bacterial Strains and Culture Conditions

Cloning and vector constructs were maintained in *E. coli* DH5α cells (Invitrogen, Carlsbad, Calif.) or *E. coli* BL21 (DE3) cells (EMD Biosciences, San Diego, Calif.). *Staphylococcus aureus* (ATCC 29740) and the mastitis isolates *Streptococcus agalactiae, S. chronogenes, S. epidermis, S. hyicus, S. simulans, S. warneri*, and *S. xylocus* (USDA) were grown at 37° C. in Brain Heart Infusion (DIFCO, Franklin Lakes, N.J.).

Example 2

PCR Cloning

The Amp$^R$ plasmid pTZ18R contains the phi11 endolysin on a 3 kb EcoRI fragment of the phi11 bacteriophage genome (gift from R. Jayaswal; Jayaswal et al. 1990. *J. Bacteriol.* 172: 5783-5788). The endolysin gene was subcloned into pET21a (EMD Biosciences, San Diego, Calif.) via PCR of pTZ18R plasmid template. High fidelity PCR (Deep Vent Polymerase; New England Biolabs, Ipswich, Mass.) with primers that introduce unique restriction enzyme (RE) sites NdeI (CATATG, includes an ATG translation initiation site), and XhoI (at the translational stop sequence, amino acid 481) were used to amplify the full length phi11 endolysin coding sequences (phi11-481). Two primers, each with the following sequences: forward primer LytA NdeI, 5'-GTG GCG CATATG CAA GCA AAA TTA AC-3' (SEQ ID NO:7) and reverse primer LytA Xho1481 5'-T GAC TAT GTC CTCGAG ACT GAT TTC-3' (SEQ ID NO:8) were used for amplification; introduced RE sites are underlined. These sites were designed to allow subcloning into pET21a such that a six Histidine tag (in pET21a) was added at the C-terminus of the phi11 protein. Gradient thermocycling determined optimal primer annealing temperature and PCR conditions. Gel-purified (Qiaex, Qiagen, Valencia, Calif.) PCR products were digested, desalted (Micro Bio-Spin 30 columns) (BioRad, Hercules, Calif.), or gel-purified and ligated to a similarly digested, dephosphorylated (Shrimp Alkaline Phosphatase, Roche, Basel, Switzerland), and purified recipient vector (pET21a) using standard techniques. In order to subclone truncated phi11 endolysin protein coding sequences, two reverse primers which introduce XhoI sites at amino acid 194 and 389 were utilized, namely, reverse primer LytA XhoI194: 5'-ACT ACC ACG CTCGAG TAG GTC-3' (SEQ ID NO:9) and reverse primer LytA XhoI389: 5'-ACT ACC ATA TTT CTCGAG TTT CCA TGC-3' (SEQ ID NO:10) with the NdeI forward primer (LytA NdeI, supra). These primers create a truncated protein coding sequence, that when cloned into pET21a, results in the truncated phi11 endolysin being fused to the 6× His tag codons of the pET21a vector. *E. coli* DH5α (Invitrogen, Carlsbad, Calif.) were transformed with the resulting ligated coding sequences. The DNA was isolated (Qiagen, Valencia, Calif.), and restriction enzyme sites mapped. BL21(DE3) *E. coli* (EMD Biosciences, San Diego, Calif.) were transformed with the characterized ligated coding sequences and the expressed protein products were purified. All constructs tested positive for peptidoglycan hydrolase activity (in lieu of DNA sequence analysis).

Figure 2:
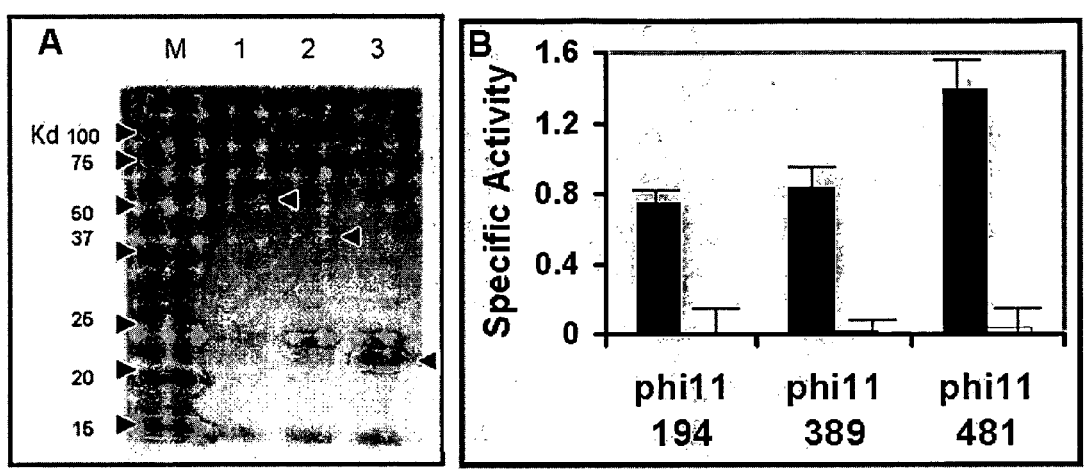
FIGS. 2A and 2B depict SDS PAGE and turbidity assay results of full length and phi11 endolysin truncations.

The full length (481 codon) phi11 endolysin protein coding region was subcloned between the NdeI and XhoI sites of pET21a. All constructs described in this work were derived from this parental clone (FIG. 1). A series of C-terminal deletions were created in order 1) to reduce the amount of protein engineering necessary to express a bacterial protein in a eukaryotic system, and 2) to determine if the SH3b domain was essential for pathogen lysis, as preparation for our goal of expressing the phi11 endolysin in transgenic cattle mammary glands. The C-terminal truncation phi11-194, contains the entire CHAP domain, bisects the amidase domain, and lacks the SH3b domain. The phi11-389 construct contains both the CHAP domain and the amidase domain, but lacks the SH3b domain. Preparations of full length and truncated gene products, partially purified on nickel columns, are visualized in SDS-PAGE (FIG. 2A). The truncations and the full length protein each lyse. *S. aureus* as shown in turbidity assays (FIG. 2B). None of the constructs were lytic towards *S. agalactiae* (FIG. 2B).

The ability of the truncated phi11-194 containing the complete CHAP domain to lyse *S. aureus* in the absence of the amidase domain is consistent with the peptidoglycan hydrolase activity of a previously described phi11 endolysin deletion whereby the amidase domain was removed from the center of the protein, resulting in the fusion of the phi11 CHAP domain to the SH3b cell wall binding domain (Navarre et al., supra). Characterization of the phi11-194 construct indicates that the CHAP domain does not require either the amidase domain or the SH3b domain for exolysis ('lysis from without') of the target bacteria. However, the intact phi11-481 protein has significantly greater activity, than either the phi11-194 or phi11-389 truncations, suggesting that although the SH3b domain may not be essential, its presence does improve the exolytic activity.

The phi11-389 construct has slightly higher exolytic activity compared to phi11-194, suggesting that the amidase domain does contribute to exolysis of *S. aureus*. Such results are in contrast to the Acm (acetylmuramidase) "mid-protein" domain of the streptococcal bacteriophage B30 endolysin which is essentially silent during exolysis of streptococci (Donovan et al. 2006b, supra).

Example 3

Extract Preparation and Protein Purification

*E. coli* BL21(DE3) cells harboring plasmid constructs were grown in 500 ml Superbroth (Becton Dickenson, Franklin Lakes, N.J.) supplemented with 100 ug/ml ampicillin at 37° C. with shaking. At mid log phase ($OD_{600nm}$ of 0.4-0.6), cultures were induced with 1 mM IPTG (isopropyl-beta-D-thiogalactopyranoside) followed by four hours shaking at 37° C. Cells were pelleted, washed with lysis buffer (50 mM $NaH_2PO_4$, 300 mM NaCl, 10 mM Imidazole, pH 8) and pellets frozen at −80° C. Extracts were prepared according to a modified procedure of Pritchard et al. (2004. Microbiology 150: 2079-2087). For nickel column-purified protein, cell pellets from 500 ml cultures were resuspended in 10 ml lysis buffer (50 mM $NaH_2PO_4$, 300 mM NaCl, 10 mM Imidazole, pH 8) and disrupted with 15×10 second pulses of sonication on ice with 10 second rest periods between pulses. Lysates were centrifuged at 6800 rpm in a Sorvall HS4 rotor (8500×g) and the supernatant decanted and added to 5 ml Ni-NTA (nickel matrix) slurry per manufacturer's instructions (Qiagen, Valencia, Calif.) with gentle rocking for 1 hour at 4° C. The matrix was washed and protein eluted according to the manufacturer's instructions. Protein eluates were desalted in Micro Bio-Spin 30 columns (BioRad) prior to protein determination with BCA protein assay (Pierce, Rockford, Ill.). The various protein fractions and Kaleidoscope protein standards (Invitrogen, Carlsbad, Calif.) were analyzed by SDS-polyacrylamide gel electrophoresis (SDS-PAGE). Proteins were loaded on 15% SDS-polyacrylamide gels and run in Tris-Glycine buffer at 131 volts for 1.5 hours in the BioRad Mini-PROTEAN 3 gel apparatus, according to the manufacturer's instructions. Gels were stained in BioSafe Coomassie stain (BioRad, Hercules, Calif.) for one hour and then rinsed in distilled water overnight.

Figure 3:
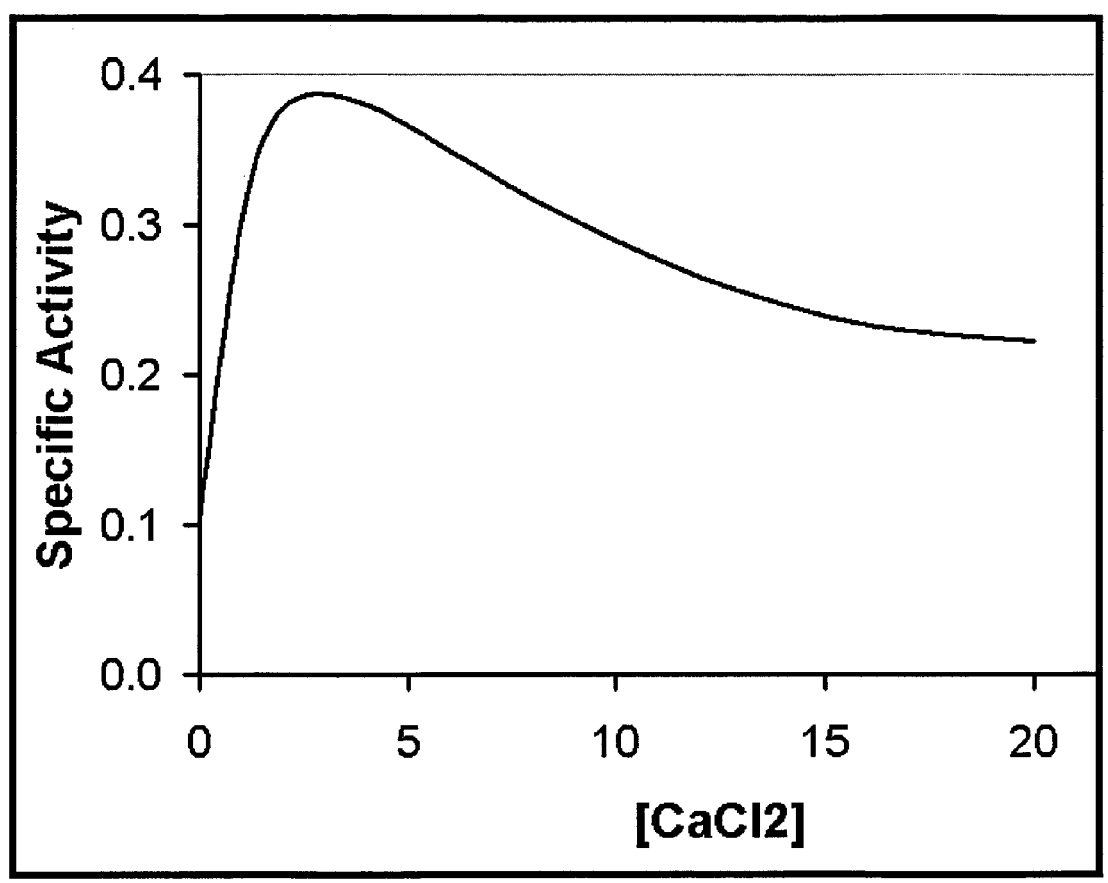
FIG. 3 shows the effect of $CaCl_2$ concentration on lytic activity of phi11-481 endolysin. Specific Activity=$OD_{600nm}$/mg/min. The graph is a representative plot. 25 µg endolysin per sample.
Figure 4:
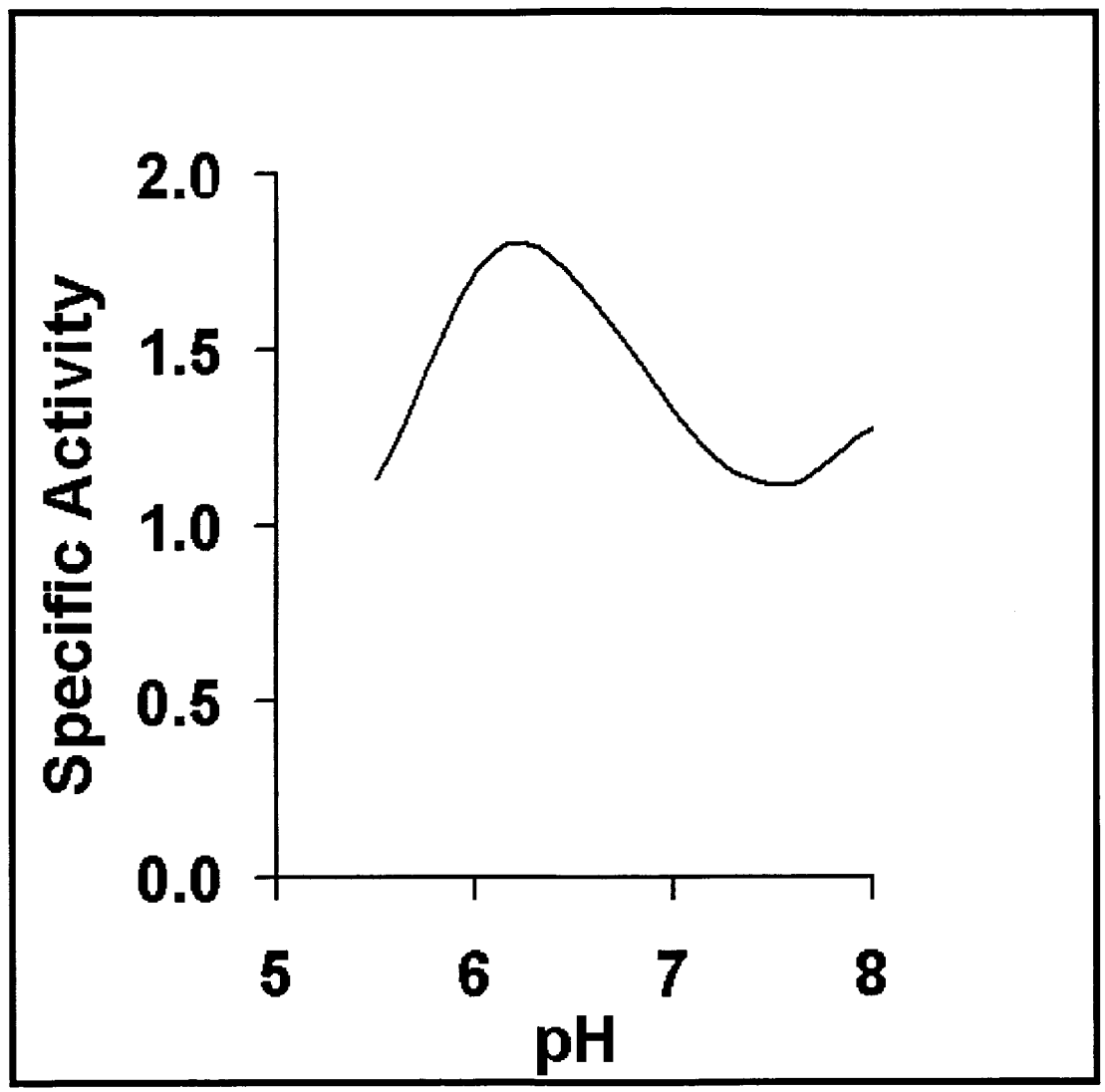
FIG. 4 shows the effect of pH on lytic activity of phi11-481 endolysin targeting *S. aureus*. Specific Activity=$OD_{600nm}$/mg/min. The graph is a representative plot. 25 µg endolysin per sample.

The phi11 endolysin is active at the physiological pH and free calcium concentration of milk. The physiological pH and free calcium concentration of bovine milk is 6.7 and 3 mM, respectively (http://www.foodsci.uoguelph.ca/dairyedu/chem.html#overview; Neville et al., supra). The phi11-481 endolysin is active at a broad range of physiologically relevant pHs (FIG. 3), and has peak activity in the turbidity assay at 2-3 mM $CaCl_2$ (FIG. 4).

Example 4

Turbidity Assay

The turbidity assay measures the drop in optical density (OD) resulting from lysis of the target bacteria with the phage endolysin-derived protein. Mid log phase ($OD_{600nm}$ of 0.4-0.6) target cells were grown in Brain Heart Infusion (Becton Dickenson, Franklin Lakes, N.J.) and concentrated in lysing buffer A (LBA; 50 mM ammonium acetate, 10 mM $CaCl_2$, 1 mM DTT at pH 6.2) to an $OD_{600nm}$ of ~2.0. Turbidity assays were performed in a cuvette containing 25 ug of partially purified phi11 endolysin-derived proteins. The turbidity assay was then initiated by addition of target cells to yield a final $OD_{600nm}$ of ~1.2 at room temperature. Changes in OD were recorded for 1 hour. Changes in the $OD_{600nm}$ in the control sample (cells alone) were subtracted from samples containing both cells and lysin, before calculating the activity (change in $OD_{600nm}$/mg protein/min). Optimum pH and Ca++ concentration were determined with modified LBA. Changes in pH were performed with glacial acetic acid or ammonium hydroxide. $CaCl_2$ was added at the appropriate concentrations to LBA lacking $CaCl_2$. Results are reported as "representative" plots due to the instability of the phi11-derived proteins and the resulting high degree of variability from assays performed on different days. However, the trends identified were consistent between the multiple preparations.

Figure 5:
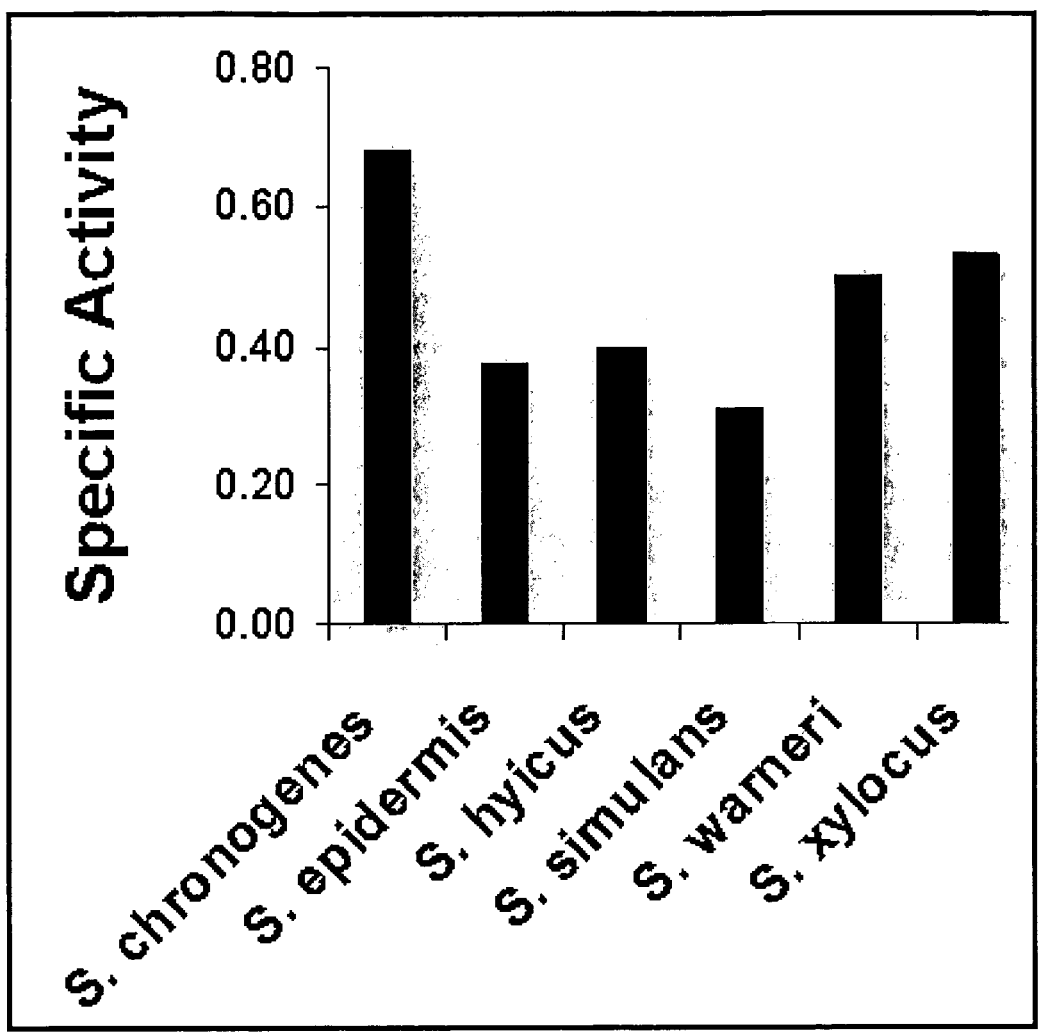
FIG. 5 depicts the turbidity assay results of phi11-481 endolysin lysis of coagulase negative staphylococci (CNS). Specific Activity=$OD_{600nm}$/mg/min. 25 µg endolysin per sample.

Phi11 endolysin is lytic towards coagulase-negative staphylococci (CNS). CNS has been reported to contribute to 11% of the mastitis cases in one study from Pennsylvania and New York (Wilson et al., supra), and to 12% of the cases in another study, where *S. simulans* accounted for 53% of the 149 CNS isolates (Waage et al. 1999. *J. Dairy Sci.* 82: 712-719). The phi11-481 endolysin is lytic for six representative strains (including *S. simulans*) that had been isolated from mastitis infections (USDA); identity was verified via the University of MD College Park microbiology service (FIG. 5).

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

I claim:

1. An isolated or recombinant nucleic acid encoding an antimicrobial phi11 endolysin-derived peptidoglycan hydrolase enzyme molecule having specificity and exolytic activity for the peptidoglycan cell wall of untreated *Staphylococcus aureus* and coagulase negative staphylococci (CNS), said CNS comprising *S. chronogenes, S. epidermis, S. hyicus, S. simulans, S. warneri*, and *S. xylocus*, wherein said phi11 endolysin-derived peptidoglycan hydrolase is a truncated peptidoglycan hydrolase having endopeptidase and amidase activity and lacking a SH3b binding domain, and said nucleic acid encoding said truncated peptidoglycan hydrolase molecule has the sequence set forth in SEQ ID NO: 2.

2. An isolated or recombinant nucleic acid encoding an antimicrobial phi11 endolysin-derived peptidoglycan hydrolase enzyme molecule having specificity and exolytic activity for the peptidoglycan cell wall of untreated *Staphylococcus aureus* and coagulase negative staphylococci (CNS), said CNS comprising *S. chronogenes, S. epidermis, S. hyicus, S. simulans, S. warneri*, and *S. xylocus*, wherein said phi11 endolysin-derived peptidoglycan hydrolase is a truncated peptidoglycan hydrolase having endopeptidase activity and lacking a SH3b binding domain, and said nucleic acid encoding said truncated peptidoglycan hydrolase molecule has the sequence set forth in SEQ ID NO: 3.

3. A construct comprising the nucleic acid of claim 1, wherein said nucleic acid is in operable linkage to a promoter that drives expression in a host cell.

4. A cloning vector comprising the construct of claim 3.

5. An expression vector comprising the construct of claim 3.

6. A process for transforming a host cell, comprising stably integrating the nucleic acid of claim 1 or the construct of claim 9 into the host cell.

7. An isolated host cell transformed with the nucleic acid according to claim 1.

8. An isolated host cell transformed with the construct according to claim 3.

9. A method of making a recombinant antimicrobial peptidoglycan hydrolase protein having endopeptidase and amidase activity and lacking a SH3b binding domain, said method comprising steps:
   a. introducing into a host cell a nucleic acid or construct encoding a antimicrobial phi11 endolysin-derived peptidoglycan hydrolase enzyme molecule having specificity and exolytic activity for the peptidoglycan cell wall of untreated *Staphylococcus aureus* and coagulase negative staphylococci (CNS), said CNS comprising *S. chronogenes, S. epidermis, S. hyicus, S. simulans, S. warneri*, and *S. xylocus*, wherein said phi11 endolysin-derived peptidoglycan hydrolase is a truncated peptidoglycan hydrolase having endopeptidase and amidase activity and lacking a SH3b binding domain, and said nucleic acid encoding said truncated peptidoglycan hydrolase molecule has the sequence set forth in SEQ ID NO:2;
   b. culturing said cell under conditions suitable for expression of said protein;
   c. recovering the protein so expressed.

* * * * *